(12) United States Patent
Kath et al.

(10) Patent No.: US 7,071,337 B2
(45) Date of Patent: Jul. 4, 2006

(54) BENZOIMIDAZOLE DERIVATIVES USEFUL AS ANTIPROLIFERATIVE AGENTS

(75) Inventors: John C. Kath, Waterford, CT (US); Joseph P. Lyssikatos, Superior, CO (US); Huifen Faye Wang, Waterford, CT (US)

(73) Assignee: Pfizer Inc, New York, NY (US)

( * ) Notice: Subject to any disclaimer, the term of this patent is extended or adjusted under 35 U.S.C. 154(b) by 371 days.

(21) Appl. No.: 10/648,151

(22) Filed: Aug. 26, 2003

(65) Prior Publication Data

US 2005/0124599 A1   Jun. 9, 2005

Related U.S. Application Data

(60) Provisional application No. 60/417,047, filed on Oct. 8, 2002, provisional application No. 60/406,524, filed on Aug. 28, 2002.

(51) Int. Cl.
*C07D 215/38* (2006.01)
*A61K 31/47* (2006.01)

(52) U.S. Cl. .................. 546/159; 514/313; 514/314

(58) Field of Classification Search ............... 514/313, 514/314; 546/159
See application file for complete search history.

(56) References Cited

FOREIGN PATENT DOCUMENTS

| WO | 0140217 | | 6/2001 |
|---|---|---|---|
| WO | WO 01/40214 | * | 6/2001 |

OTHER PUBLICATIONS

Palmer BD et al. Journal of Medicinal Chemistry, vol. 42, 1999, pp. 2373-2382, XP002157335.
Palmer BD et al. Journal of Medicinal Chemistry, vol. 41, 1998, pp. 5457-5465, XP002157336.

* cited by examiner

*Primary Examiner*—D. Margaret Seaman
(74) *Attorney, Agent, or Firm*—Steve T. Zelson; Sandra Kim

(57) ABSTRACT

The invention relates to compounds of the formula 1

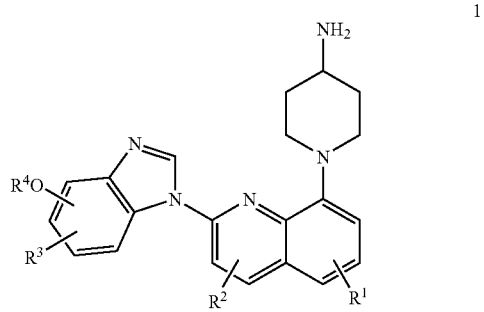

and to pharmaceutically acceptable salts, prodrugs and solvates thereof, wherein $R^1$, $R^2$, $R^3$, and $R^4$ are as defined herein. The invention also relates to methods of treating abnormal cell growth, such as cancer, in mammals by administering the compounds of formula 1 and to pharmaceutical compositions for treating such disorders which contain the compounds of formula 1. The invention also relates to methods of preparing the compounds of formula 1.

9 Claims, No Drawings

BENZOIMIDAZOLE DERIVATIVES USEFUL AS ANTIPROLIFERATIVE AGENTS

BACKGROUND OF THE INVENTION

This invention relates to novel benzimidazole derivatives that are useful in the treatment of abnormal cell growth, such as cancer, in mammals. This invention also relates to a method of using such compounds in the treatment of abnormal cell growth in mammals, especially humans, and to pharmaceutical compositions containing such compounds.

It is known that a cell may become cancerous by virtue of the transformation of a portion of its DNA into an oncogene (i.e., a gene which, on activation, leads to the formation of malignant tumor cells). Many oncogenes encode proteins that are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are enzymes which span the cell membrane and possess an extracellular binding domain for growth factors such as epidermal growth factor, a transmembrane domain, and an intracellular portion which functions as a kinase to phosphorylate specific tyrosine residues in proteins and hence to influence cell proliferation. Other receptor tyrosine kinases include c-erbB-2, c-met, tie-2, PDGFr, FGFr, and VEGFR. It is known that such kinases are frequently aberrantly expressed in common human cancers such as breast cancer, gastrointestinal cancer such as colon, rectal or stomach cancer, leukemia, and ovarian, bronchial or pancreatic cancer. It has also been shown that epidermal growth factor receptor (EGFR), which possesses tyrosine kinase activity, is mutated and/or overexpressed in many human cancers such as brain, lung, squamous cell, bladder, gastric, breast, head and neck, oesophageal, gynecological and thyroid tumors.

Accordingly, it has been recognized that inhibitors of receptor tyrosine kinases are useful as selective inhibitors of the growth of mammalian cancer cells. For example, erbstatin, a tyrosine kinase inhibitor, selectively attenuates the growth in athymic nude mice of a transplanted human mammary carcinoma that expresses epidermal growth factor receptor tyrosine kinase (EGFR) but is without effect on the growth of another carcinoma that does not express the EGF receptor. Thus, the compounds of the present invention, which are selective inhibitors of certain receptor tyrosine kinases, in particular PDGFr, are useful in the treatment of abnormal cell growth, in particular cancer, in mammals.

Various other compounds, such as styrene derivatives, have also been shown to possess tyrosine kinase inhibitory properties. More recently, five European patent publications, namely EP 0 566 226 A1 (published Oct. 20, 1993), EP 0 602 851 A1 (published Jun. 22, 1994), EP 0 635 507 A1 (published Jan. 25, 1995), EP 0 635 498 A1 (published Jan. 25, 1995), and EP 0 520 722 A1 (published Dec. 30, 1992), refer to certain bicyclic derivatives, in particular quinazoline derivatives, as possessing anti-cancer properties that result from their tyrosine kinase inhibitory properties. Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published Mar. 6, 1996), WO 97/30034 (published Aug. 21, 1997), WO 98/02434 (published Jan. 22, 1998), WO 98/02437 (published Jan. 22, 1998), and WO 98/02438 (published Jan. 22, 1998), also refer to substituted bicyclic heteroaromatic derivatives as tyrosine kinase inhibitors that are useful for the same purpose. Also see WO 99/16755, *J. Med. Chem.* 1998, 41, 5457–5465 and *J. Med. Chem.* 1999, 42, 2373–2382.

SUMMARY OF THE INVENTION

The present invention relates to compounds of the formula 1

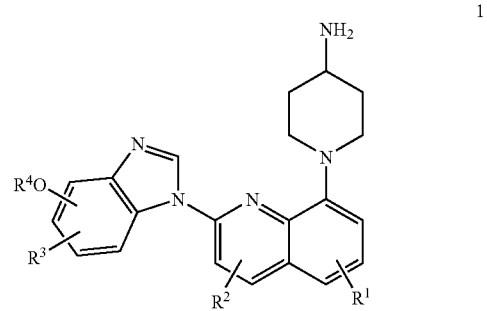

or a pharmaceutically acceptable salt, prodrug, hydrate or solvate thereof, wherein each $R^1$, $R^2$, and $R^3$ is independently selected from H, $C_1$–$C_6$ alkyl, $C_3$–$C_6$ cycloalkyl, halo, cyano, $CF_3$, difluoromethoxy, trifluoromethoxy, $OC_1$–$C_6$ alkyl, $OC_3$–$C_6$ cycloalkyl, and $NR^7R^8$;

wherein $R^4$ is —$(CR^5R^6)_n$H, or —$(CR^5R^6)_m$(4 to 10 membered heterocyclic), wherein n is an integer ranging from 1 to 5, wherein m is an integer ranging from 0 to 5, wherein said 4 to 10 membered heterocyclic when aromatic is optionally substituted by 1 to 3 $R^1$ substituents, and wherein said 4 to 10 membered heterocyclic when non-aromatic is optionally substituted by 1 to 3 $R^7$ substituitents at any position and optionally substituted by 1 to 3 $R^9$ substituents at any position not adjacent to or directly attached to a heteroatom;

wherein each $R^5$ and $R^6$ is independently selected from H or $C_1$–$C_6$ alkyl;

wherein each $R^7$ and $R^8$ is independently selected from H, $C_1$–$C_6$ alkyl, and $C_3$–$C_6$ cycloalkyl; and wherein each $R^9$ is independently selected from halo, cyano, $CF_3$, difluoromethoxy, trifluoromethoxy, $OC_1$–$C_6$ alkyl, $OC_3$–$C_6$ cycloalkyl, and $NR^7R^8$.

In another embodiment of the present invention each $R^1$, $R^2$, and $R^3$ is independently selected from H, $C_1$–$C_6$ alkyl, and $C_3$–$C_6$ cycloalkyl, halo, and cyano.

In one embodiment of the present invention $R^4$ is —$(CR^5R^6)_m$H.

In a preferred embodiment, the present invention relates to compounds of the formula 1a

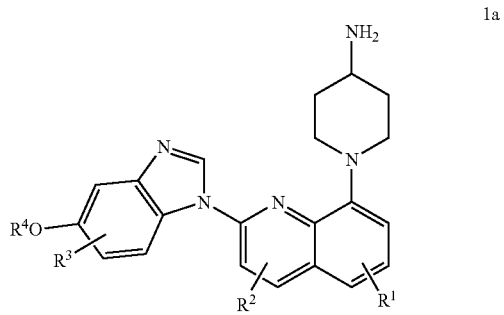

or a pharmaceutically acceptable salt, prodrug, hydrate or solvate thereof, wherein each $R^1$, $R^2$, and $R^3$ is independently selected from H, $C_1$–$C_6$ alkyl, $C_3$–$C_6$ cycloalkyl, halo, cyano, $CF_3$, difluoromethoxy, trifluoromethoxy, $OC_1$–$C_6$ alkyl, $OC_3$–$C_6$ cycloalkyl, and $NR^7R^8$;

wherein $R^4$ is —$(CR^5R^6)_nH$, or —$(CR^5R^6)_m$(4 to 10 membered heterocyclic), wherein n is an integer ranging from 1 to 5, wherein m is an integer ranging from 0 to 5, wherein said 4 to 10 membered heterocyclic when aromatic is optionally substituted by 1 to 3 $R^1$ substituents, and wherein said 4 to 10 membered heterocyclic when non-aromatic is optionally substituted by 1 to 3 $R^7$ substituitents at any position and optionally substituted by 1 to 3 $R^9$ substituents at any position not adjacent to or directly attached to a heteroatom;

wherein each $R^5$ and $R^6$ is independently selected from H or $C_1$–$C_6$ alkyl;

wherein each $R^7$ and $R^8$ is independently selected from H, $C_1$–$C_6$ alkyl, and $C_3$–$C_6$ cycloalkyl; and wherein each $R^9$ is independently selected from halo, cyano, $CF_3$, difluoromethoxy, trifluoromethoxy, $OC_1$–$C_6$ alkyl, $OC_3$–$C_6$ cycloalkyl, and $NR^7R^8$.

In another embodiment of the present invention $R^4$ is —$(CR^5R^6)_m$(4 to 10 membered heterocyclic), wherein m is an integer ranging from 0 to 5 and wherein said 4 to 10 membered heterocyclic group is optionally substituted by 1 to 3 $R^7$ substituitents at any position and optionally substituted by 1 to 3 $R^9$ substituents at any position not adjacent to or directly attached to a heteroatom.

In another embodiment of the present invention $R^4$ is —$(CH_2)_m$(4 to 10 membered heterocyclic), wherein m is an integer ranging from 0 to 3 and wherein said 4 to 10 membered heterocyclic group is optionally substituted by 1 to 3 $R^7$ substituitents at any position and optionally substituted by 1 to 3 $R^9$ substituents at any position not adjacent to or directly attached to a heteroatom.

The invention further relates to compounds of formula 1 or 1a, wherein $R^4$ is —$(CH_2)_m$(4 to 10 membered heterocyclic), wherein m is an integer ranging from 0 to 3 and wherein said 4 to 10 membered heterocyclic group is optionally substituted by 1 to 2 $R^7$ substituitents at any position and optionally substituted by 1 to 3 $R^9$ substituents at any position not adjacent to or directly attached to a heteroatom.

The invention further relates to compounds of formula 1 or 1a, wherein $R^4$ is —$(CH_2)_m$(4 to 10 membered heterocyclic), wherein m is an integer ranging from 0 to 2 and wherein said 4 to 10 membered heterocyclic group is optionally substituted by 1 $R^7$ substituitent at any position and optionally substituted by 1 to 3 $R^9$ substituents at any position not adjacent to or directly attached to a heteroatom.

The invention also relates to compounds of formula 1 or 1a, wherein $R^4$ is —$(CH_2)_m$(4 to 10 membered heterocyclic), wherein m is 1 and wherein said 4 to 10 membered heterocyclic group is optionally substituted by 1 $R^7$ substituitent at any position and optionally substituted by 1 to 3 $R^9$ substituents at any position not adjacent to or directly attached to a heteroatom.

The invention also relates to compounds of formula 1 or 1a, wherein $R^4$ is —$(CH_2)_m$(4 to 8 membered heterocyclic), wherein m is 1 and wherein said 4 to 8 membered heterocyclic group is optionally substituted by 1 $R^7$ substituitent at any position and optionally substituted by 1 to 3 $R^9$ substituents at any position not adjacent to or directly attached to a heteroatom.

The invention further relates to compounds of formula 1 or 1a, wherein $R^4$ is —$(CH_2)_m$(4 to 6 membered heterocyclic), wherein m is 1 and wherein said 4 to 6 membered heterocyclic group is optionally substituted by 1 $R^7$ substituitent at any position and optionally substituted by 1 to 2 $R^9$ substituents at any position not adjacent to or directly attached to a heteroatom.

In a preferred embodiment the invention relates to compounds of formula 1 or 1a, wherein $R^4$ is —$(CH_2)_m$(6 membered heterocyclic), wherein m is 1 and wherein said 6 membered heterocyclic group is optionally substituted by 1 $R^7$ substituitent at any position and optionally substituted by 1 $R^9$ substituent at any position not adjacent to or directly attached to a heteroatom.

In a more preferred embodiment the invention relates to compounds of formula 1 or 1a, wherein $R^4$ is —$(CH_2)_m$(5 membered heterocyclic), wherein m is 1 and wherein said 5 membered heterocyclic group is optionally substituted by 1 $R^7$ substituitent at any position and optionally substituted by 1 $R^9$ substituent at any position not adjacent to or directly attached to a heteroatom.

In a most preferred embodiment the invention relates to compounds of formula 1 or 1a, wherein $R^4$ is —$(CH_2)_m$(4 membered heterocyclic), wherein m is 1 and wherein said 4 membered heterocyclic group is optionally substituted by 1 $R^7$ substituitent at any position and optionally substituted by 1 $R^9$ substituent at any position not adjacent to or directly attached to a heteroatom.

In a preferred embodiment the present invention relates to compounds of formula 1 or 1a, wherein said 4 to 10 membered heterocyclic is selected from the group consisting of pyrrolidinyl, tetrahydrofuranyl, tetrahydropyranyl, tetrahydrothiopyranyl, morpholino, and oxetanyl.

In one embodiment the present invention relates to compounds of formula 1 or 1a, wherein $R^1$ is selected from the group consisting of H, $C_1$–$C_6$ alkyl, $C_3$–$C_6$ cycloalkyl, halo, and cyano.

In one embodiment of the present invention relates to compounds of formula 1 or 1a, wherein the $R^1$ group is $C_1$–$C_6$ alkyl selected from methyl, butyl, ethyl, propyl and pentyl.

In another embodiment of the present invention the $C_1$–$C_6$ alkyl is selected from methyl, butyl, ethyl, and propyl.

In a preferred embodiment the $R^1$ group is $C_1$–$C_6$ alkyl selected from methyl, butyl, and ethyl.

In a more preferred embodiment the $R^1$ group is methyl.

In another embodiment of the present invention each $R^5$ and $R^6$ of the compound of formula 1 or 1a is independently selected from methyl, ethyl, propyl and butyl.

In a preferred embodiment each $R^5$ and $R^6$ is independently selected from methyl, and ethyl.

In a more preferred embodiment each $R^5$ and $R^6$ is methyl.

In another specific embodiment of the present invention $R^4$ is —$(CR^5R^6)_m$(4 to 8 membered heterocyclic), wherein m is an integer ranging from 0 to 3 and wherein said 4 to 8 membered heterocyclic group is optionally substituted by 1 to 3 $R^7$ substituitents at any position and optionally substituted by 1 to 3 $R^9$ substituents at any position not adjacent to or directly attached to a heteroatom.

In another specific embodiment of the present invention $R^4$ is —$(CR^5R^6)_m$(4 to 6 membered heterocyclic), wherein m is an integer ranging from 0 to 3 and wherein said 4 to 10 membered heterocyclic group is optionally substituted by 1 to 3 $R^7$ substituitents at any position and optionally substituted by 1 to 3 $R^9$ substituents at any position not adjacent to or directly attached to a heteroatom.

In another specific embodiment of the present invention $R^4$ is —$(CR^5R^6)_m$(6 membered heterocyclic), wherein m is an integer ranging from 0 to 3 and wherein said 6 membered heterocyclic group is optionally substituted by 1 to 3 $R^7$ substituitents at any position and optionally substituted by 1 to 3 $R^9$ substituents at any position not adjacent to or directly attached to a heteroatom.

In another specific embodiment of the present invention $R^4$ is —$(CR^5R^6)_m$(5 membered heterocyclic), wherein m is an integer ranging from 0 to 2 and wherein said 5 membered heterocyclic group is optionally substituted by 1 to 3 $R^7$ substituitents at any position and optionally substituted by 1 to 3 $R^9$ substituents at any position not adjacent to or directly attached to a heteroatom.

In another specific embodiment of the present invention $R^4$ is —$(CR^5R^6)_m$(4 membered heterocyclic), wherein m is an integer ranging from 0 to 2 and wherein said 4 membered heterocyclic group is optionally substituted by 1 to 3 $R^7$ substituitents at any position and optionally substituted by 1 to 3 $R^9$ substituents at any position not adjacent to or directly attached to a heteroatom.

In another specific embodiment of the present invention the heterocylic group of $R^4$ contains one to four heteroatoms each selected from O, S and N, with the proviso that the 4 to 10 membered heterocyclic ring does not contain two adjacent O or S atoms.

In another specific embodiment of the present invention heterocylic group of $R^4$ contains one to four O atoms with the proviso that the ring does not contain two adjacent O atoms.

In another specific embodiment of the present invention the heterocylic group of $R^4$ contains one to two O atoms with the proviso that the ring does not contain two adjacent O atoms.

In another specific embodiment of the present invention the heterocylic group of $R^4$ contains one O atom.

In another specific embodiment of the present invention the heterocylic group of $R^4$ contains one to four N atoms.

In another specific embodiment of the present invention the heterocylic group of $R^4$ contains one to two N atoms.

In another specific embodiment of the present invention the heterocylic group of $R^4$ contains one N atom.

In another specific embodiment of the present invention the $R^4$ is —$(CR^5R^6)_m$(4 to 10 membered non-aromatic heterocyclic), wherein m is an integer ranging from 0 to 1 and wherein said 4 to 10 membered heterocyclic group is optionally substituted by 1 to 3 $R^7$ substituitents at any position and optionally substituted by 1 to 3 $R^9$ substituents at any position not adjacent to or directly attached to a heteroatom.

In another specific embodiment of the present invention the $R^4$ is —$(CR^5R^6)_m$(4 to 8 membered non-aromatic heterocyclic), wherein m is an integer ranging from 0 to 1 and wherein said 4 to 8 membered non-aromatic heterocyclic group is optionally substituted by 1 to 3 $R^7$ substituitents at any position and optionally substituted by 1 to 3 $R^9$ substituents at any position not adjacent to or directly attached to a heteroatom.

In another specific embodiment of the present invention the $R^4$ is —$(CR^5R^6)_m$(4 to 6 membered non-aromatic heterocyclic), wherein m is an integer ranging from 0 to 1 and wherein said 4 to 6 membered non-aromatic heterocyclic group is optionally substituted by 1 to 3 $R^7$ substituitents at any position and optionally substituted by 1 to 3 $R^9$ substituents at any position not adjacent to or directly attached to a heteroatom.

In another specific embodiment of the present invention the $R^4$ is —$(CR^5R^6)_m$(6 membered non-aromatic heterocyclic), wherein m is an integer ranging from 0 to 1 and wherein said 6 membered non-aromatic heterocyclic group is optionally substituted by 1 to 3 $R^7$ substituitents at any position and optionally substituted by 1 to 3 $R^9$ substituents at any position not adjacent to or directly attached to a heteroatom.

In another specific embodiment of the present invention the $R^4$ is —$(CR^5R^6)_m$(5 membered non-aromatic heterocyclic), wherein m is an integer ranging from 0 to 1 and wherein said 5 membered non-aromatic heterocyclic group is optionally substituted by 1 to 3 $R^7$ substituitents at any position and optionally substituted by 1 to 3 $R^9$ substituents at any position not adjacent to or directly attached to a heteroatom.

In another specific embodiment of the present invention the $R^4$ is —$(CR^5R^6)_m$(4 membered non-aromatic heterocyclic), wherein m is an integer ranging from 0 to 1 and wherein said 4 membered non-aromatic heterocyclic group is optionally substituted by 1 to 3 $R^7$ substituitents at any position and optionally substituted by 1 to 3 $R^9$ substituents at any position not adjacent to or directly attached to a heteroatom.

In another specific embodiment of the present invention said 4 to 10 membered heterocyclic is selected from the group consisting of azetidinyl, thiazolyl, quinolinyl, pyrrolidinyl, tetrahydrofuranyl, tetrahydrothienyl, tetrahydropyranyl, tetrahydrothiopyranyl, piperidino, morpholino, thiomorpholino, piperazinyl, homopiperazinyl, oxetanyl, homopiperidinyl, indolinyl, dioxanyl, 3-azabicyclo[3.1.0]hexanyl, 3-azabicyclo[4.1.0]heptanyl, azabicyclo[2.2.2]hexanyl, and 3H-indolyl.

In another specific embodiment of the present invention the 4 to 10 membered heterocyclic is selected from the group consisting of pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

In another specific embodiment of the present invention said 4 to 10 membered heterocyclic is selected from the group consisting of pyrrolidinyl, tetrahydrofuranyl, tetrahydropyranyl, tetrahydrothiopyranyl, piperidino, morpholino, piperazinyl, homopiperazinyl, azetidinyl, oxetanyl, homopiperidinyl, 3-azabicyclo[3.1.0]hexanyl, 3-azabicyclo[4.1.0]heptanyl, azabicyclo[2.2.2]hexanyl, 3H-indolyl and quinolizinyl.

In another specific embodiment of the present invention said 4 to 10 membered heterocyclic is selected from the group consisting of pyrrolidinyl, tetrahydrofuranyl, tetrahydropyranyl, tetrahydrothiopyranyl, morpholino, and oxetanyl.

In another specific embodiment of the present invention said 4 to 10 membered heterocyclic is selected from the group consisting of tetrahydrofuranyl, tetrahydropyranyl, tetrahydrothiopyranyl, morpholino, and oxetanyl.

In another embodiment of the present invention $R^4$ is —$(CR^5R^6)_m$(4 to 10 membered heterocyclic), wherein m is an integer ranging from 0 to 5 and wherein said 4 to 10 membered heterocyclic group is optionally substituted by 1 to 3 $R^1$ substituents.

In another embodiment of the present invention $R^4$ is —$(CH_2)_m$(4 to 10 membered heterocyclic), wherein m is an integer ranging from 0 to 3 and wherein said 4 to 10 membered heterocyclic group is optionally substituted by 1 to 3 $R^1$ substituents.

The invention further relates to compounds of formula 1 or 1a, wherein $R^4$ is —$(CH_2)_m$(4 to 10 membered heterocyclic), wherein m is an integer ranging from 0 to 3 and wherein said 4 to 10 membered heterocyclic group is optionally substituted by 1 to 2 $R^1$ substituents.

The invention further relates to compounds of formula 1 or 1a, wherein $R^4$ is —$(CH_2)_m$(4 to 10 membered heterocyclic), wherein m is an integer ranging from 0 to 2 and wherein said 4 to 10 membered heterocyclic group is optionally substituted by 1 $R^1$ substituent.

The invention also relates to compounds of formula 1 or 1a, wherein $R^4$ is —$(CH_2)_m$(4 to 10 membered heterocyclic), wherein m is 1 and wherein said 4 to 10 membered heterocyclic group is optionally substituted by 1 $R^1$ substituent.

The invention also relates to compounds of formula 1 or 1a, wherein $R^4$ is —$(CH_2)_m$(4 to 8 membered heterocyclic), wherein m is 1 and wherein said 4 to 8 membered heterocyclic group is optionally substituted by 1 $R^1$ substituent.

The invention further relates to compounds of formula 1 or 1a, wherein $R^4$ is —$(CH_2)_m$(4 to 6 membered heterocyclic), wherein m is 1 and wherein said 4 to 6 membered heterocyclic group is optionally substituted by 1 $R^1$ substituent.

In a preferred embodiment the invention relates to compounds of formula 1 or 1a, wherein $R^4$ is —$(CH^2)_m$(6 membered heterocyclic), wherein m is 1 and wherein said 6 membered heterocyclic group is optionally substituted by 1 $R^1$ substituent.

In a more preferred embodiment the invention relates to compounds of formula 1 or 1a, wherein $R^4$ is —$(CH_2)_m$(5 membered heterocyclic), wherein m is 1 and wherein said 5 membered heterocyclic group is optionally substituted by 1 $R^1$ substituent.

In a most preferred embodiment the invention relates to compounds of formula 1 or 1a, wherein $R^4$ is —$(CH^2)_m$(4 membered heterocyclic), wherein m is 1 and wherein said 4 membered heterocyclic group is optionally substituted by 1 $R^1$ substituent.

In another specific embodiment of the present invention $R^4$ is —$(CR^5R^6)_m$(4 to 8 membered heterocyclic), wherein m is an integer ranging from 0 to 3 and wherein said 4 to 8 membered heterocyclic group is optionally substituted by 1 to 3 $R^1$ substituents.

In another specific embodiment of the present invention $R^4$ is —$(CR^5R^6)_m$(4 to 6 membered heterocyclic), wherein m is an integer ranging from 0 to 3 and wherein said 4 to 6 membered heterocyclic group is optionally substituted by 1 to 3 $R^1$ substituents.

In another specific embodiment of the present invention $R^4$ is —$(CR^5R^6)_m$(6 membered heterocyclic), wherein m is an integer ranging from 0 to 3 and wherein said 6 membered heterocyclic group is optionally substituted by 1 to 3 $R^1$ substituents.

In another specific embodiment of the present invention $R^4$ is —$(CR^5R^6)_m$(5 membered heterocyclic), wherein m is an integer ranging from 0 to 2 and wherein said 5 membered heterocyclic group is optionally substituted by 1 to 3 $R^1$ substituents.

In another specific embodiment of the present invention $R^4$ is —$(CR^5R^6)_m$(4 membered heterocyclic), wherein m is an integer ranging from 0 to 2 and wherein said 4 membered heterocyclic group is optionally substituted by 1 to 3 $R^1$ substituents.

In another specific embodiment of the present invention said 4 to 10 membered heterocyclic is selected from the group consisting of tetrahydrofuranyl, morpholino, oxetanyl, and 4H-pyranyl.

Preferred compounds include those selected from the group consisting of:

1-{2-[5-(3-Morpholin-4-yl-propoxy)-benzoimidazol-1-yl]-quinolin-8-yl}-piperidin-4-ylamine;

(±)-1-{2-[5-(Tetrahydro-furan-3-yloxy)-benzoimidazol-1-yl]-quinolin-8-yl}-piperidin-4-ylamine;

1-{2-[5-(3-Methyl-oxetan-3-ylmethoxy)-benzoimidazol-1-yl]-quinolin-8-yl}-piperidin-4-ylamine;

1-[2-(5-Isobutoxy-benzoimidazol-1-yl)-quinolin-8-yl]-piperidin-4-ylamine;

1-{2-[5-(Tetrahydro-pyran-4-yloxy)-benzoimidazol-1-yl]-quinolin-8-yl}-piperidin-4-ylamine; and the pharmaceutically acceptable salts, prodrugs, hydrates and solvates of the foregoing compounds.

In one preferred embodiment the compound is selected from the group consisting of:

1-{2-[5-(3-Morpholin-4-yl-propoxy)-benzoimidazol-1-yl]-quinolin-8-yl}-piperidin-4-ylamine;

(+)-1-{2-[5-(Tetrahydro-furan-3-yloxy)-benzoimidazol-1-yl]-quinolin-8-yl}-piperidin-4-ylamine;

(−)-1-{2-[5-(Tetrahydro-furan-3-yloxy)-benzoimidazol-1-yl]-quinolin-8-yl}-piperidin-4-ylamine; and the pharmaceutically acceptable salts, prodrugs, hydrates and solvates of the foregoing compounds.

In another preferred embodiment the compound is selected from the group consisting of 1-{2-[5-(3-Morpholin-4-yl-propoxy)-benzoimidazol-1-yl]-quinolin-8-yl}-piperidin-4-ylamine; and the pharmaceutically acceptable salts, prodrugs, hydrates and solvates of the foregoing compound.

In another preferred embodiment the compound is selected from the group consisting of 1-{2-[5-(3-Methyl-oxetan-3-ylmethoxy)-benzoimidazol-1-yl]-quinolin-8-yl}-piperidin-4-ylamine; and the pharmaceutically acceptable salts, prodrugs, hydrates and solvates of the foregoing compound.

In another preferred embodiment the compound is selected from the group consisting of 1-[2-(5-Isobutoxy-benzoimidazol-1-yl)-quinolin-8-yl]-piperidin-4-ylamine; and the pharmaceutically acceptable salts, prodrugs, hydrates and solvates of the foregoing compound.

In another preferred embodiment the compound is selected from the group consisting of 1-{2-[5-(Tetrahydro-pyran-4-yloxy)-benzoimidazol-1-yl]-quinolin-8-yl}-piperidin-4-ylamine; and the pharmaceutically acceptable salts, prodrugs, hydrates and solvates of the foregoing compound.

In one preferred embodiment the compound of the present invention is the benzenesulfonate salt of any of the aforementioned compounds.

The invention also relates to a method for the treatment of abnormal cell growth in a mammal comprising administering to said mammal an amount of a compound of formula 1 or 1a that is effective in treating abnormal cell growth.

In one preferred embodiment of the present invention the abnormal cell growth is cancer.

In one embodiment of the present invention the cancer is selected from lung cancer, bone cancer, pancreatic cancer, gastric, skin cancer, cancer of the head or neck, cutaneous or intraocular melanoma, uterine cancer, ovarian cancer, gynecological, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, squamous cell, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain, pituitary adenoma, or a combination of one or more of the foregoing cancers.

In a preferred embodiment of the present invention the cancer is selected from the group consisting of brain, squamous cell, bladder, gastric, pancreatic, breast, head, neck, oesophageal, prostate, colorectal, lung, renal, kidney, ovarian, gynecological and thyroid cancer.

In a preferred embodiment of the present invention the cancer is selected from the group consisting of prostate, breast, lung, colon and ovarian cancer.

In another preferred embodiment of the present invention the cancer is selected from the group consisting of prostate, breast, and lung cancer.

In a more preferred embodiment the breast cancer is metastatic breast cancer.

In a more preferred embodiment the lung cancer is non-small cell lung cancer.

In another embodiment of the present invention the abnormal cell growth is non-cancerous.

In one embodiment of the present invention the non-cancerous abnormal cell growth is benign hyperplasia of the skin or prostate.

The invention also relates to a method for the treatment of vasculogenesis, restenosis, atherosclerosis or angiogenesis in a mammal comprising administering to said mammal a therapeutically effective amount of a compound of formula 1 or 1a, or a pharmaceutically acceptable salt, prodrug or hydrate 1 that is effective in treating vasculogenesis, restenosis, atherosclerosis or angiogenesis.

In one preferred embodiment of the present invention relates a method for treating a disease related to vasculogenesis or angiogenesis.

In one embodiment of the present invention relates to a method for the treatment of a hyperproliferative disorder in a mammal which comprises administering to said mammal a therapeutically effective amount of a compound of formula 1 or 1a, or a pharmaceutically acceptable salt, prodrug or hydrate in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

The invention also relates to a pharmaceutical composition for the treatment of abnormal cell growth in a mammal comprising an amount of a compound of formula 1 or 1 a that is effective in treating abnormal cell growth, and a pharmaceutically acceptable carrier.

In one embodiment of the present invention the pharmaceutical composition of formula 1 or 1a is use for treating abnormal cell growth such as cancer.

The invention further relates to a process of preparing a compound of the formula 1

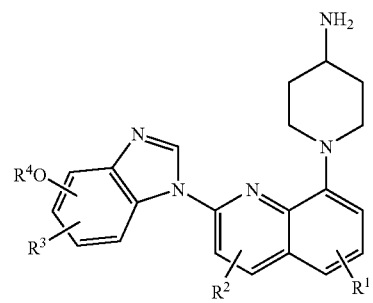

or a pharmaceutically acceptable salt, prodrug, hydrate or solvate thereof, wherein each $R^1$, $R^2$, and $R^3$ is independently selected from H, $C_1$–$C_6$ alkyl, $C_3$–$C_6$ cycloalkyl, halo, cyano, $CF_3$, difluoromethoxy, trifluoromethoxy, $OC_1$–$C_6$ alkyl, $OC_3$–$C_6$ cycloalkyl, and $NR^7R^8$;

wherein $R^4$ is —$(CR^5R^6)_nH$, or —$(CR^5R^6)_m$(4 to 10 membered heterocyclic), wherein n is an integer ranging from 1 to 5, wherein m is an integer ranging from 0 to 5, wherein said 4 to 10 membered heterocyclic when aromatic is optionally substituted by 1 to 3 $R^1$ substituents, and wherein said 4 to 10 membered heterocyclic when non-aromatic is optionally substituted by 1 to 3 $R^7$ substituitents at any position and optionally substituted by 1 to 3 $R^9$ substituents at any position not adjacent to or directly attached to a heteroatom;

wherein each $R^5$ and $R^6$ is independently selected from H or $C_1$–$C_6$ alkyl wherein each $R^7$ and $R^8$ is independently selected from H, $C_1$–$C_6$ alkyl, and $C_3$–$C_6$ cycloalkyl; and wherein each $R^9$ is independently selected from halo, cyano, $CF_3$, difluoromethoxy, trifluoromethoxy, $OC_1$–$C_6$ alkyl, $OC_3$–$C_6$ cycloalkyl, and $NR^7R^8$, which comprises treating a compound of the formula 2

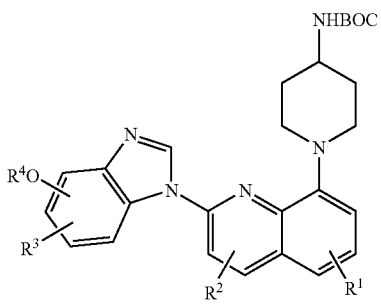

with an acid to give a compound of the formula 1.

The invention also relates to a pharmaceutical composition for the treatment of a hyperproliferative disorder in a mammal which comprises a therapeutically effective amount of a compound of formula 1 or 1a, or a pharmaceutically acceptable salt, prodrug or hydrate thereof, and a pharmaceutically acceptable carrier. In one embodiment, said pharmaceutical composition is for the treatment of cancer such as brain, lung, squamous cell, bladder, gastric, pancreatic, breast, head, neck, renal, kidney, ovarian, prostate, colorectal, oesophageal, testicular, gynecological or thyroid cancer. In another embodiment, said pharmaceutical composition is for the treatment of a non-cancerous hyperproliferative disorder such as benign hyperplasia of the skin (e.g., psoriasis), restenosis, or prostate (e.g., benign prostatic hypertropy (BPH)).

The invention also relates to a pharmaceutical composition for the treatment of pancreatitis or kidney disease (including proliferative glomerulonephritis and diabetes-induced renal disease) in a mammal which comprises a therapeutically effective amount of a compound of formula 1 or 1a, or a pharmaceutically acceptable salt, prodrug or hydrate thereof, and a pharmaceutically acceptable carrier.

The invention also relates to a pharmaceutical composition for the prevention of blastocyte implantation in a mammal that comprises a therapeutically effective amount of a compound of formula 1 or 1a, or a pharmaceutically acceptable salt, prodrug or hydrate thereof, and a pharmaceutically acceptable carrier.

The invention also relates to a pharmaceutical composition for treating a disease related to vasculogenesis, restenosis, atherosclerosis or angiogenesis in a mammal which comprises a therapeutically effective amount of a compound of formula 1 or 1a, or a pharmaceutically acceptable salt, prodrug or hydrate thereof, and a pharmaceutically acceptable carrier. In one embodiment, said pharmaceutical composition is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal that comprises administering to said mammal a therapeutically effective amount of the compound of formula 1 or 1a, or a pharmaceutically acceptable salt, prodrug or hydrate thereof. In one embodiment, said method relates to the treatment of cancer such as brain, squamous cell, bladder, gastric, pancreatic, breast, head, neck, oesophageal, prostate, colorectal, lung, renal, kidney, ovarian, testicular, gynecological or thyroid cancer. In another embodiment, said method relates to the treatment of a non-cancerous hyperproliferative disorder such as benign hyperplasia of the skin (e.g., psoriasis), restenosis or prostate (e.g., benign prostatic hypertropy (BPH)).

The invention also relates to a method for the treatment of a hyperproliferative disorder in a mammal which comprises administering to said mammal a therapeutically effective amount of a compound of formula 1 or 1a, or a pharmaceutically acceptable salt, prodrug or hydrate in combination with a therapeutically effective amount of an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

The invention also relates to a method of treating pancreatitis or kidney disease in a mammal which comprises administering to said mammal a therapeutically effective amount of a compound of formula 1 or 1 a, or a pharmaceutically acceptable salt, prodrug or hydrate thereof.

The invention also relates to a method of preventing blastocyte implantation in a mammal which comprises administering to said mammal a therapeutically effective amount of a compound of formula 1 or 1a, or a pharmaceutically acceptable salt, prodrug or hydrate thereof.

The invention also relates to a method of treating diseases related to vasculogenesis or angiogenesis in a mammal which comprises administering to said mammal an effective amount of a compound of formula 1 or 1a, or a pharmaceutically acceptable salt, prodrug or hydrate thereof. In one embodiment, said method is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with a compounds of formula 1 or 1a, and the pharmaceutically acceptable salts, prodrugs and hydrates of said compounds, according to the methods of this invention include, for example, patients that have been diagnosed as having psoriasis, restenosis, atherosclerosis, BPH, lung cancer, bone cancer, CMML, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, testicular, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g, cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

This invention also relates to a pharmaceutical composition for inhibiting abnormal cell growth in a mammal which comprises an amount of a compound of formula 1 or 1a, or a pharmaceutically acceptable salt or solvate or prodrug thereof, in combination with an amount of a chemotherapeutic, wherein the amounts of the compound, salt, solvate, or prodrug, and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, e.g. anti-androgens.

This invention further relates to a method for inhibiting abnormal cell growth in a mammal or treating a hyperproliferative disorder which method comprises administering to the mammal an amount of a compound of formula 1 or 1a, or a pharmaceutically acceptable salt or solvate or prodrug thereof, in combination with radiation therapy, wherein the amount of the compound, salt, solvate or prodrug is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

It is believed that the compounds of formula 1 or 1a can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of formula 1 or 1a or pharmaceutically acceptable salt, prodrug or solvate thereof, which amount is effective in sensitizing abnormal cells to treatment with radiation. The amount of the compound, salt, or solvate in this method can be determined according to the means for ascertaining effective amounts of such compounds described herein.

This invention also relates to a method of and to a pharmaceutical composition for inhibiting abnormal cell growth in a mammal which comprises an amount of a compound of formula 1 or 1a, a pharmaceutically acceptable salt or solvate thereof, a prodrug thereof, or an isotopically-labelled derivative thereof, and an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX-II (cyclooxygenase 11) inhibitors, can be used in conjunction with a compound of formula 1 or 1a and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed June 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and the compounds recited in the following list:

3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonylamino]-8-oxa-bicyclo[3.2.1]octane-3-carboxylic acid hydroxyamide;

(2R, 3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran-4-carboxylic acid hydroxyamide;

(R) 3-[4-(4-chloro-phenoxy)-benzenesulfonylamino]-tetrahydro-pyran-3-carboxylic acid hydroxyamide;

(2R, 3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide;

and pharmaceutically acceptable salts and solvates of said compounds.

Other anti-angiogenesis agents, including other COX-II inhibitors and other MMP inhibitors, can also be used in the present invention.

A compound of formula 1 or 1a, can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225, anti-EGFR$^{22}$Mab (ImClone Systems Incorporated of New York, N.Y., USA), and ABX-EGF (Abgenix antibody) the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.). These and other EGFR-inhibiting agents can be used in the present invention.

VEGF inhibitors, for example SU-5416 and SU-6668 (Sugen Inc. of South San Francisco, Calif., USA), can also be combined with the compound of the present invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No.

5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8,1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); IMC-1C11 Imclone antibody, anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as GW-282974 (Glaxo Wellcome plc), and the monoclonal antibodies AR-209 (Aronex Pharmaceuticals Inc. of The Woodlands, Texas, USA) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the compound of the present invention in accordance with the present invention.

The compound of the invention can also be used with other agents useful in treating abnormal cell growth or cancer, including, but not limited to, agents capable of enhancing antitumor immune responses, such as CTLA4 (cytotoxic lymphocite antigen 4) antibodies, and other agents capable of blocking CTLA4; and anti-proliferative agents such as farnesyl protein transferase inhibitors, and $\alpha v \beta 3$ inhibitors, such as the $\alpha v \beta 3$ antibody Vitaxin, and $\alpha v \beta 5$ inhibitors and the like. Specific CTLA4 antibodies that can be used in the present invention include those described in U.S. Provisional Application 60/113,647 (filed Dec. 23, 1998) which is incorporated by reference in its entirety, however other CTLA4 antibodies can be used in the present invention.

The compounds of formula 1 or 1a and their pharmaceutically acceptable salts, prodrugs and solvates can each independently also furthermore be used in a palliative neoadjuvant/adjuvant therapy in alleviating the symptoms associated with the diseases recited herein as well as the symptoms associated with abnormal cell growth. Such therapy can be a monotherapy or can be in a combination with chemotherapy and/or immunotherapy.

The invention also relates to a method of preparing a compound of the formula 1

The terms "abnormal cell growth" and "hyperproliferative disorder" are used interchangeably in this application.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The term "Me" means methyl, "Et" means ethyl, and "Ac" means acetyl.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight, branched, or cyclic moieties (including fused and bridged bicyclic and spirocyclic moieties), or a combination of the foregoing moieties. For an alkyl group to have cyclic moieties, the group must have at least three carbon atoms.

The term "cycloalkyl", as used herein, unless otherwise indicated, includes cyclic alkyl moieties wherein alkyl is as defined above. The use of the term "cycloalkyl" shall not be construed as limiting the term "alkyl" to non-cyclic moieties.

The term "alkenyl", as used herein, unless otherwise indicated, includes alkyl moieties having at least one carbon-carbon double bond wherein alkyl is as defined above and including E and Z isomers of said alkenyl moiety.

The term "alkynyl", as used herein, unless otherwise indicated, includes alkyl moieties having at least one carbon-carbon triple bond wherein alkyl is as defined above.

The term "alkoxy", as used herein, unless otherwise indicated, includes O-alkyl groups wherein alkyl is as defined above.

The term "aryl", as used herein, unless otherwise indicated, includes an organic radical derived from an aromatic hydrocarbon by removal of one hydrogen, such as phenyl or naphthyl.

The term "4 to 10 membered heterocyclic", as used herein, unless otherwise indicated, includes aromatic and non-aromatic heterocyclic groups containing one to four heteroatoms each selected from O, S and N, wherein each heterocyclic group has from 4–10 atoms in its ring system, and with the proviso that the ring of said group does not contain two adjacent O or S atoms. Non-aromatic heterocyclic groups include groups having only 4 atoms in their ring system, but aromatic heterocyclic groups must have at least 5 atoms in their ring system. The heterocyclic groups include benzo-fused ring systems. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyclo[3.1.0]hexanyl, 3-azabicyclo[4.1.0]heptanyl, azabicyclo[2.2.2]hexanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition including 1-oxa-6-aza-spiro[2.5]oct-6-yl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl.

The phrase "pharmaceutically acceptable salt(s)", as used herein, unless otherwise indicated, includes salts of acidic or basic groups which may be present in the compounds of formula 1 or 1a. The compounds of formula 1 or 1a that are basic in nature are capable of forming a wide variety of salts with various inorganic and organic acids. The acids that may be used to prepare pharmaceutically acceptable acid addition salts of such basic compounds of formula 1 or 1a are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methysulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts. Since a single compound of the present invention may include more than one acidic or basic moieties, the compounds of the present invention may include mono, di or tri-salts in a single compound.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

The present invention includes within its scope prodrugs of the compounds of formula 1 or 1a above. In general, such prodrugs will be functional derivatives of the compounds of formula 1 or 1a which are readily convertible in vivo into the required compound of formula 1 or 1a. Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The compounds according to the invention have one or more asymmetric centres, and may accordingly exist both as enantiomers and as diastereoisomers. It is to be understood that all such isomers and mixtures thereof are encompassed within the scope of the present invention.

In the compounds of formula 1 or 1a, where terms such as $(CR^4R^5)_m$ or $(CR^4R^5)_t$ are used, $R^4$ and $R^5$ may vary with each iteration of m or t above 1. For instance, where m or t is 2, the terms $(CR^4R^5)_m$ or $(CR^4R^5)_t$ may equal —$CH_2CH_2$—, or —$CH(CH_3)C(CH_2CH_3)(CH_2CH_2CH_3)$—, or any number of similar moieties falling within the scope of the definitions of $R^4$ and $R^5$.

Certain compounds of formula 1 or 1a may have asymmetric centers and therefore exist in different enantiomeric forms. All optical isomers and stereoisomers of the compounds of formula 1 or 1a, and mixtures thereof, are considered to be within the scope of the invention. With respect to the compounds of formula 1 or 1a, the invention includes the use of a racemate, one or more enantiomeric forms, one or more diastereomeric forms, or mixtures thereof. The compounds of formula 1 or 1a may also exist as tautomers. This invention relates to the use of all such tautomers and mixtures thereof.

The subject invention also includes isotopically-labelled compounds, which are identical to those recited in formula 1 or 1a, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula 1 or 1a of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing and methods of treating proliferative disorders, or abnormal cell growth, by administering prodrugs of compounds of the formula 1 or 1a. Compounds of formula 1 or 1a having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1 or 1a. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethy-loxycarbonys, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

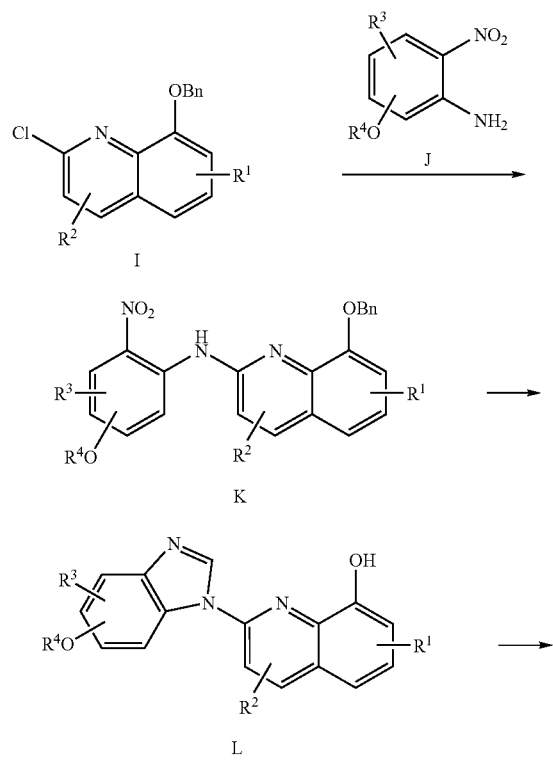

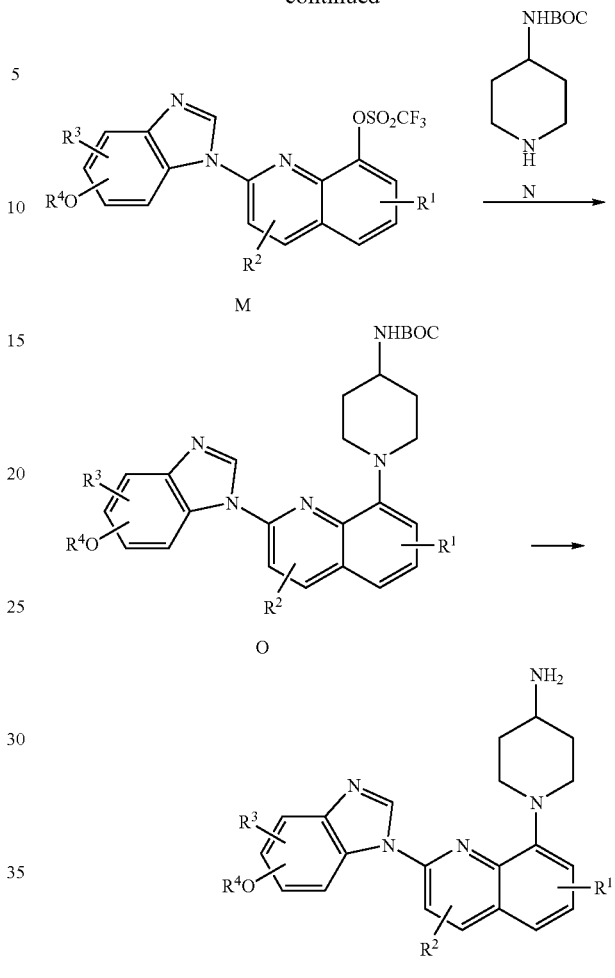

DETAILED DESCRIPTION OF THE INVENTION

General synthetic methods which may be referred to for preparing the compounds of the present invention are provided in U.S. Pat. No. 5,990,146 (issued Nov. 23, 1999) (Warner-Lambert Co.) and PCT published application numbers WO 99/16755 (published Apr. 8, 1999)(Merck & Co.) and WO 01/40217 (published Jul. 7, 2001)(Pfizer, Inc.). The foregoing patent and patent applications are hereby incorporated by reference in their entirety.

The compounds of this invention may alternatively be prepared according to the scheme 1 from 2-chloro-8-benzyloxyquinoline (I) and an appropriate 2-amino-nitrobenzene (J) by the method outlined in Scheme 1. The substituents $R^1$, $R^2$, $R^3$ and $R^4$ are as defined for the compounds of formula 1 or 1a in the summary of the invention. Palladium catalyzed amination of I and J provides quinoline K. Reduction of the nitro group and removal of the benzyl group via catalytic hydrogenation provides the benzimidazole L which can then be transformed into the corresponding triflate M. A second palladium catalyzed amination with amine N provides piperidinyl quinoline O and subsequent removal of the t-butyloxycarbonyl group provides the desired product 1.

The compounds of the present invention may have asymmetric carbon atoms. Diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention.

The compounds of formula 1 or 1a are basic in nature and are capable of forming a wide variety of different salts with various inorganic and organic acids. Although such salts must be pharmaceutically acceptable for administration to animals, it is often desirable in practice to initially isolate the compound of formula 1 or 1a from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

The activity of the compounds of formula 1 or 1a may be determined by the following procedure.

General PGT Kinase ELISA Method

The following reagent and stock solutions are used:

| | |
|---|---|
| adenosine triphosphate (ATP) | Sigma, cat. # A-2383 |
| bovine serum albumin (BSA) | Sigma, cat. # A-3294 |
| Dulbecco's PBS (dPBS) | Gibco-BRL, cat. # 14190-136 |
| MaxiSorp plates | Nunc, cat. # 439454 |
| $MgCl_2$ | Sigma, cat. # M-1028 |
| Poly-Glu-Tyr (PGT) | Sigma, cat. #. P-0275 |
| TMB Micowell Substrate | Kirkegaard & Perry, cat. # 50-76-05 |
| Tween 20 | Sigma, cat. # P-1379 |
| HRP-PY54 antibody | OSI Pharmaceuticals, Inc. |

Phosphorylation Buffer (PB): 50 mM HEPES, pH 7.3, 125 mM NaCl, 24 mM $MgCl_2$;
Wash Buffer (WB): dPBS + 0.1% Tween 20 (polyoxyethylene sorbitan); and
Blocking Buffer: 3% BSA, 0.05% Tween 20 in dPBS.

Assay Procedure:

(a) For plate coating, fill Nunc MaxiSorp plate with 100 µl per well of Poly-Glu-Tyr (PGT) diluted in dPBS (various concentrations). The plate is the incubated overnight at 37° C. The supernatant PGT is then disgarded, and the plates are washed 3× with Wash Buffer.

(b) The PDGF enzyme is then diluted in PB to an appropriate concentration, and 25 µl of this stock solution is added per well.

(c) ATP is then diluted (from 20 mM stock) to an appropriate concentration (0.5 nM-2 uM) with PB. The phosphorylation reaction is commenced by addition of 25 µl ATP solution to each well of the assay plate. Incubation is continued for about 10 minutes, with shaking at room temperature.

(d) The reaction is stopped by aspirating off the reaction mixture. The plate is then washed 4× with WB.

(e) The HRP-PY54 antibody is diluted to an appropriate concentration in blocking buffer. 50 µl of this solution is then added per well, followed by incubation for 25–35 minutes at room temperature. The antibody-containing solution is aspirated away, and the plate is again washed 4× with WB.

(f) The extent of reaction is determined by measurement of light absorbance at 450 nm. First, color is developed by addition of TMB solution, 50 µl per well, and the reaction is permitted to run until wells with positive signals achieve about 0.6–1.2 OD450 units. Color development is then stopped by addition of 50 µl per well of 0.09 M H2SO4. The background controls are wells without PGT, but with all other components included. As aforementioned, preferred signal is generally in the range of 0.6–1.2 OD units, with essentially no background.

The in vitro activity of the compounds of the present invention in inhibiting the PDGF□ receptor may be determined by the following procedure.

Inhibition of tyrosine kinase activity may be measured using a recombinant enzyme in an assay that measures the ability of compounds to inhibit the phosphorylation of the exogenous substrate, polyGluTyr (PGT, Sigma™, 4:1). The cytoplasmic domain of the human PDGFβ receptor (amino acids 559–1106) (Ishikawa, F., et al. Nature 338: 557–562, 1989) is expressed in Sf9 insect cells as a glutathione S-transferase (GST)-fusion protein using the baculovirus expression system. The protein is then purified from the lysates of these cells using glutathione agarose affinity columns.

The enzyme assay is performed in 96-well plates that are coated with the PGT substrate (0.625 µg PGT per well). Test compounds are diluted in dimethylsulfoxide (DMSO), and then added to the PGT plates so that the final concentration of DMSO in the assay is 1.6% (v/v). The recombinant enzyme is diluted in phosphorylation buffer (50 mM Hepes, pH 7.3, 125 mM NaCl, 24 mM $MgCl_2$). The reaction is initiated by the addition of ATP to a final concentration of 10 µM. After a 10 minute incubation at room temperature with shaking, the reaction is aspirated, and the plates are washed with wash buffer (PBS-containing 0.1% Tween-20). The amount of phosphorylated PGT is quantitated by incubation with a horseradish peroxidase(HRP)-conjugated PY-54 antibody (Transduction Labs), developing with TMB peroxidase (TMB is 3,3',5,5'-tetramethylbenzidine), and detection on a BioRad™ Microplate reader at 450 nM. Inhibition of the kinase enzymatic activity by the test compound is detected as a reduced absorbance, and the concentration of the compound that is required to inhibit the signal by 50% (under the circumstances of the assay) is reported as the $IC_{50}$ value for the test compound.

To measure the ability of the compounds to inhibit PDGFRβ tyrosine kinase activity for the full length protein that exists in a cellular context, the porcine aortic endothelial (PAE) cells transfected with the human PDGFRβ (Westermark, Bengt, et. al., PNAS 87, pp128–132, 1990) may be used. Cells are plated and allowed to attach to 96-well dishes in the same media (Ham's F12) with 10% FBS (fetal bovine serum) for 6–8 hours. The cells are washed, re-fed with serum depleted media, and allowed to incubate over night. Immediately prior to dosing with compound, the cells are re-fed with the serum depleted media. Test compounds, dissolved in DMSO, are diluted into the media (final DMSO concentration 0.5% (v/v)). At the end of a 10 minutes incubation, PDGF-BB (100 ng/ml final) is added to the media for an 8 minute incubation. The cells are washed with Hepes buffered saline solution (HBSS) and lysed in 50 ul of HNTG buffer (20 mM Hepes, pH 7.5, 150 mM NaCl, 0.2% Triton™ X-100, 10% glycerol, plus 0.2 mM PMSF (phenymethylsulfonyl fluoride), 1 µg/ml pepstatin, 1 µg/ml leupeptin, 1 µg/ml aprotonin, 2 mM sodium pyrophosphate, 2 mM sodium orthovanadate) and then diluted with 50 ul of HG dilution buffer (20 mM Hepes, pH 7.5, 10% glycerol, 0.2 mM PMSF (phenymethylsulfonyl fluoride), 1 µg/ml pepstatin, 1 µg/ml leupeptin, 1 µg/ml aprotonin, 2 mM sodium pyrophosphate, 2 mM sodium orthovanadate). The extent of phosphorylation of PDGFRβ is measured using an ELISA assay. The 96-well Protein A coated plates are blocked with Superblock (Pierce) and coated with 0.5 µg per well anti-PDGFRβ P20 antibody (Santa Cruz, catalog number SC-339).

Any unbound antibody is washed off the plates prior to addition of the cell lysate. After a 2 hour room temperature incubation of the lysates (50 ul) with the PDGFRβ antibody, the PDGFRβ associated phosphotyrosine is quantitated by development with the HRP-conjugated PY-54 antibody and TMB, as described above. The ability of the compounds to inhibit the PDGF-BB stimulated autophosphorylation reaction by 50% under the conditions used, relative to PDGF-BB-stimulated controls, is reported as the $IC_{50}$ value for the test compound. The compounds of the present invention, including the examples recited below, generally have IC50 values using the foregoing procedure falling within the following range: 1–1000 nM.

The in vitro activity of the compounds of the present invention in inhibiting the KDR/VEGF receptor may be determined by the following procedure.

The ability of the compounds of the present invention to inhibit tyrosine kinase activity may be measured using a recombinant enzyme in an assay that measures the ability of compounds to inhibit the phosphorylation of the exogenous substrate, polyGluTyr (PGT, Sigma™, 4:1). The kinase domain of the human KDR/VEGF receptor (amino acids 805–1350) is expressed in Sf9 insect cells as a glutathione S-transferase (GST)-fusion protein using the baculovirus expression system. The protein is purified from the lysates of these cells using glutathione agarose affinity columns. The enzyme assay is performed in 96-well plates that are coated with the PGT substrate (0.625 µg PGT per well). Test compounds are diluted in dimethylsulfoxide (DMSO), and then added to the PGT plates so that the final concentration of DMSO in the assay is 1.6% (v/v). The recombinant enzyme is diluted in phosphorylation buffer (50 mM Hepes, pH 7.3, 125 mM NaCl, 24 mM $MgCl_2$). The reaction is initiated by the addition of ATP to a final concentration of 10 µM. After a 30 minute incubation at room temperature with shaking, the reaction is aspirated, and the plates are washed with wash buffer (PBS-containing 0.1% Tween-20). The amount of phosphorylated PGT is quantitated by incubation with a HRP-conjugated (HRP is horseradish peroxidase) PY-54 antibody (Transduction Labs), developed with TMB peroxidase (TMB is 3,3',5,5'-tetramethylbenzidine), and the reaction is quantitated on a BioRad™ Microplate reader at 450 nM. Inhibition of the kinase enzymatic activity by the test compound is detected as a reduced absorbance, and the concentration of the compound that is required to inhibit the signal by 50% is reported as the $IC_{50}$ value for the test compound.

To measure the ability of the compounds to inhibit KDR tyrosine kinase activity for the full length protein that exists in a cellular context, the porcine aortic endothelial (PAE) cells transfected with the human KDR (Waltenberger et al., J. Biol. Chem. 269:26988, 1994) may be used. Cells are plated and allowed to attach to 96-well dishes in the same media (Ham's F12) with 10% FBS (fetal bovine serum). The cells are then washed, re-fed with serum depleted media that contains 0.1% (v/v) bovine serum albumin (BSA), and allowed to incubate for 24 hours. Immediately prior to dosing with compound, the cells are re-fed with the serum depleted media (without BSA). Test compounds, dissolved in DMSO, are diluted into the media (final DMSO concentration 0.5% (v/v)). At the end of a 2 hour incubation, $VEGF_{165}$ (50 ng/ml final) is added to the media for an 8 minute incubation. The cells are washed and lysed in HNTG buffer (20 mM Hepes, pH 7.5, 150 mM NaCl, 0.2% Triton™ X-100, 10% glycerol, 0.2 mM PMSF (phenylmethylsulfonyl fluoride), 1 µg/ml pepstatin, 1 µg/ml leupeptin, 1 µg/ml aprotonin, 2 mM sodium pyrophosphate, 2 mM sodium orthovanadate). The extent of phosphorylation of KDR is measured using an ELISA assay. The 96-well plates are coated with 1 µg per well of goat anti-rabbit antibody. Unbound antibody is washed off the plate and remaining sites are blocked with Superblock buffer (Pierce) prior to addition of the anti-flk-1 C-20 antibody (0.5 µg per plate, Santa Cruz). Any unbound antibody is washed off the plates prior to addition of the cell lysate. After a 2 hour incubation of the lysates with the flk-1 antibody, the KDR associated phosphotyrosine is quantitated by development with the HRP-conjugated PY-54 antibody and TMB, as described above. The ability of the compounds to inhibit the VEGF-stimulated autophosphorylation reaction by 50%, relative to VEGF-stimulated controls is reported as the $IC_{50}$ value for the test compound.

Human liver cytosol incubations were conducted using commercially available cryopreserved cytosol (Tissue Transformation Technologies, 20 mg/mL protein, Lot #HHC-0255). Human liver cytosol was slowly thawed and diluted in 100 mM potassium phosphate buffer (pH 7.4) to a final protein concentration of 3.1 mg/mL and warmed to 37° C. Incubations were initiated with the addition of compound stock dissolved in methanol. Total methanol concentration was kept at or below 1%. After reaction initiation, incubation was gently mixed and a 0 min sample aliquot was collected and quenched in an equal volume of acetonitrile containing an internal standard. Subsequent time points were collected at 5, 10, 15 and 30 minutes and quenched in the same manner. Samples were centrifuged and the supernatants were analyzed by HPLC/MS/MS using the ratio of the peak area response of the analyte to that of the internal standard. A linear regression was fit to the data and half-lifes were calculated from the slope of the line. The percent remaining calculations were performed using the half life of the fitted data. Control incubations were included for to monitor interday variability and non-cytosolic mediated loss. The compounds of the present invention were stable in human liver cytosal assay described above.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), intraocular, intraperitoneal, intravesicular, intravaginal, topical, and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumour substances, for example those selected from, for example, mitotic inhibitors, for example vinblastine; alkylating agents, for example cis-platin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl4-oxo-quinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

Preparation of General Intermediates

8-Benzyloxy-2-chloro-quinoline 2,8-Quinolinediol (133.3 g, 0.827 mol) was dissolved in 800 mL of anhydrous DMF under an atmosphere of dry $N_2$. To this solution was added potassium carbonate (183 g, 1.32 mol) followed by benzyl bromide (110 mL, 0.909 mol) and the solution was then warmed up to 65° C. and reacted at this temperature overnight. The reaction mixture was then poured into 9 L of water and the resulting solution was stirred at ambient temperature for 5.5 hours after which time it was filtered. The solid was washed with water, collected and suspended in toluene and finally the solution was concentrated under vacuum to give 142 g of 8-benzyloxy-quinolin-2-ol. This material (142 g, 0.565 mol) was dissolved in 500 mL of DCE under an atmosphere of dry $N_2$. Oxalyl chloride (99 mL, 1.13 mol) was added dropwise to this solution followed by 1 mL of DMF. After the addition was complete, the reaction was stirred at ambient temperature for 30 minutes after which time the reaction was warmed to 84° C. The reaction mixture was stirred at this temperature for 10 hours and then concentrated under vacuum. The resulting residue was partitioned between DCM and aqueous saturated $NaHCO_3$. The DCM layer was washed again with aqueous saturated $NaHCO_3$, dried over $Na_2SO_4$, filtered and concentrated under vacuum to give a brown solid. The solid was recrystallised from toluene to give two crops of (68.3 g and 38.3 g) of 8-benzyloxy-2-chloro-quinoline.

Piperidin-4-yl-carbamic acid tert-butyl ester can be prepared by the methods found in Carling et. Al. J. Med. Chem. 42(14), (1999) p. 2706 or Mase et. Al. J. Org. Chem. 66(20), (2001) p.6775.

Compounds of the Formula 1 or 1a may be prepared from intermediate H (Example 1) by the method outlined in Scheme 1 and exemplified by the preparation of 1-[2-(5-Cyclopropylmethoxy-benzoimidazol-1-yl)-quinolin-8-yl]-piperidin-4-ylamine in Example 2.

EXAMPLE 1

Preparation of {1-[2-(5-Hydroxy-benzoimidazol-1-yl]-quinolin-8-yl-piperidin-4-yl}-carbamic acid tert-butyl ester (compound H)

The 5-hydroxy-benzimidazole intermediate H may be prepared by the method outlined in Scheme 2.

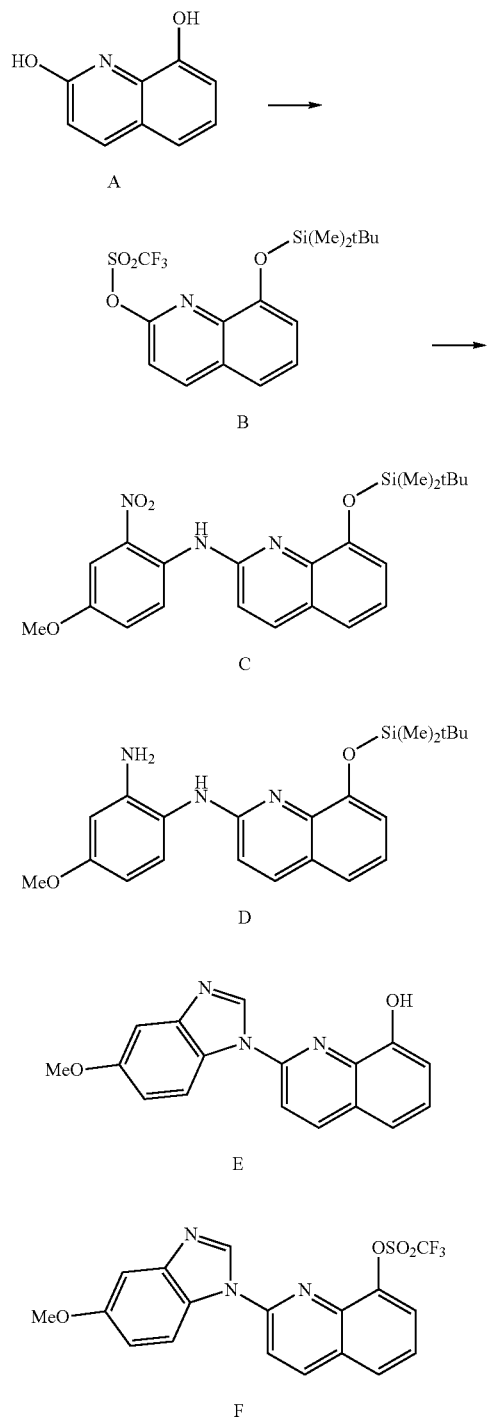

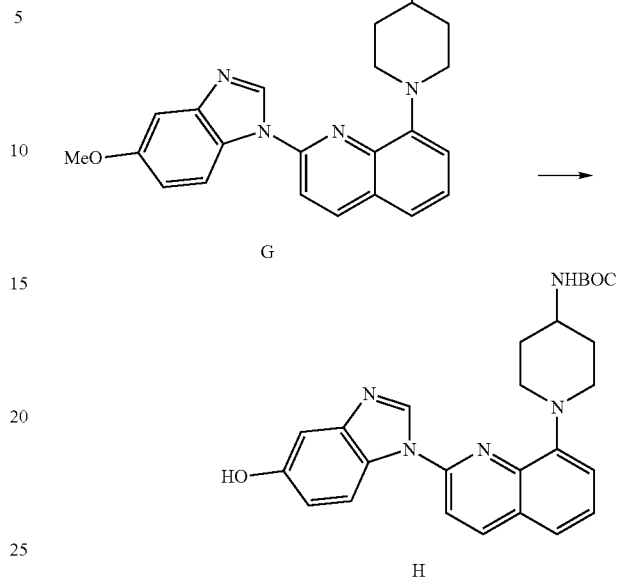

Preparation of Compound B

Trifluoro-methanesulfonic acid 8-(tert-butyl-dimethyl-silanyloxy)-quinolin-2-yl ester 2,8-Quinolinediol (A) (20.0 g, 124 mmol) was suspended in 500 mL of dichloromethane (DCM) under an atmosphere of dry nitrogen ($N_2$). To this solution was added imidazole (20.3 g, 298 mmol) followed by tert-butyldimethylsilyl chloride (20.6 9, 137 mmol) and 4-dimethylaminopyridine (1.50 g, 12.4 mmol). The reaction mixture was stirred overnight at ambient temperature after which time it was partitioned between DCM and 1% aqueous sodium bisulfate ($NaHSO_4$). The DCM layer was saved and washed two more times with 1% aqueous $NaHSO_4$, then aqueous saturated sodium bicarbonate ($NaHCO_3$) and finally brine. The DCM layer was dried over sodium sulfate ($Na_2SO_4$), filtered and concentrated under vacuum to give crude product (40 g) as a white solid. The solid was dissolved in 500 mL of anhydrous tetrahydrofuran (THF) under an atmosphere of dry $N_2$. To this solution was added N-phenyl-bis(trifluoromethanesulfonimide) (48.7 g, 136 mmol) and the solution was cooled to 0° C. To this solution was slowly added (3.2 g, 136 mmol) sodium hydride (60% in oil). After the addition was complete, the reaction mixture was warmed to ambient temperature. An additional 1.00 g sodium hydride (60% in oil) was added after one hour and stirred for an additional 30 minutes. The mixture was concentrated under vacuum and taken up in DCM. Water (1.0 mL) was slowly added dropwise to quench any unreacted sodium hydride and then the reaction mixture was extracted twice from 0.1N aqueous sodium hydroxide (NaOH) and then washed with brine. The DCM layer was dried over $Na_2SO_4$, filtered and concentrated under vacuum to give 57 g of the crude triflate B as a yellow oil.

Preparation of Compound C ([8-(tert-Butyl-dimethyl-silanyloxy)-quinolin-2-yl]-(4-methoxy-2-nitro-phenyl)-amine Trifluoro-methanesulfonic acid 8-(tert-butyl-dimethyl-silanyloxy)-quinolin-2-yl ester B (9.81 g, 24.1 mmol) and 4-methoxy-2-nitroaniline (4.86 g, 28.9 mmol) were dissolved in 100 mL of dioxane under an atmosphere of dry $N_2$. To this solution was added (11.0 g, 33.7 mmol) cesium carbonate ($Cs_2CO_3$), (900 mg, 1.45 mmol) racemic-2,2'-bis(diphenylposphino)-1,1'-binapthyl (BINAP) and tris(dibenzylideneacetone)dipalladium (0) (883 mg, 0.964 mmol) and the reaction mixture was heated to 100° C. and reacted at this temperature for 4 hours. The mixture was then cooled to ambient temperature, concentrated under vacuum, treated with DCM, filtered and concentrated under vacuum to give a red solid. The solid was chromatographed on flash silica gel eluting with hexanes/DCM (3:1) to give 7.25 g of C as a red solid.

Preparation of Compound D $N^1$-[8-(tert-Butyl-dimethyl-silanyloxy)-quinolin-2-yl]-4-methoxy-benzene-1,2-diamine ([8-(tert-Butyl-dimethyl-silanyloxy)-quinolin-2-yl]-(4-methoxy-2-nitro-phenyl)-amine C (21.9 g, 51.3 mmol) was dissolved in 200 mL ethanol (EtOH) and 70 mL of THF under an atmosphere of dry $N_2$. To this solution was added 10% palladium on carbon (2.18 g) followed by the dropwise addition of 10 mL of anhydrous hydrazine. The reaction mixture was stirred at ambient temperature for 2 hours after which time it was filtered through Celite™ and the Celite™ washed with DCM. The combined filtrates were concentrated under vacuum and the resulting residue was partitioned between DCM and aqueous saturated $NaHCO_3$. The DCM layer was then washed again with saturated $NaHCO_3$ and then brine, dried over $Na_2SO_4$, filtered and concentrated under vacuum to give 18.3 g of a tan solid as the title compound D.

Preparation of Compound E 2-(5-Methoxy-benzoimidazol-1-yl)-quinolin-8-ol $N^1$-[8-(tert-Butyl-dimethyl-silanyloxy)-quinolin-2-yl]-4-methoxy-benzene-1,2-diamine D (18.3 g, 46.1 mmol) was dissolved in 40 mL of 2-methoxyethanol under an atmosphere of dry $N_2$. To this solution was added formamidine acetate (5.28 g, 50.7 mmol) and the reaction mixture was heated to 125° C. and reacted at this temperature for 1.5 hours. The solvent was removed under vacuum and the resulting solid was triturated with ethyl ether ($Et_2O$), dried under vacuum to give 13.3 g of E as a pink solid.

Preparation of Compound F

Trifluoro-methanesulfonic acid 2-(5-methoxy-benzoimidazol-1-yl)-quinolin-8-yl ester 2-(5-Methoxy-benzoimidazol-1-yl)-quinolin-8-ol E (13.9 g, 47.8 mmol) was dissolved in 100 mL of anhydrous THF under an atmosphere of dry $N_2$. To this solution was added N-phenyl-bis(trifluoromethanesulfonimide) (20.3 g, 47.8 mmol) and then the solution was subsequently cooled to 0° C. To this solution was slowly added (1.31 9, 54.9 mmol) sodium hydride (60% in oil). After the addition was complete the reaction mixture was warmed to ambient temperature. After 30 minutes, 500 mg more of sodium hydride (60% in oil) was added followed by 3.50 g of N-phenyl-bis (trifluoromethanesulfonimide) and the reaction mixture was stirred at ambient temperature for 1 hour. The solvent was then removed under vacuum and the resulting residue was taken up in DCM. To this solution was slowly added 1.0 mL of water to decompose any unreacted sodium hydride. The mixture was subsequently partitioned between DCM and 0.1 N aqueous NaOH. The DCM layer was then washed again with 0.1 N aqueous NaOH, followed by brine and then dried over magnesium sulfate ($MgSO_4$), filtered and concentrated under vacuum to give 20.7 g of crude F as a pink solid used immediately in the next reaction.

Preparation of Compound G

{1-[2-(5-Methoxy-benzoimidazol-1-yl)-quinolin-8-yl]-piperidin-4-yl}-carbamic acid tert-butyl ester Trifluoro-methanesulfonic acid 2-(5-methoxy-benzoimidazol-1-yl)-quinolin-8-yl ester F (15.0 9, 35.4 mmol) and piperidin-4-yl-carbamic acid tert-butyl ester (14.2 9, 70.9 mmol) were dissolved in 200 mL of dioxane under an atmosphere of dry $N_2$. To this solution was added $Cs_2CO_3$ (16.2 g, 49.6 mmol), racemic-BINAP (1.28 9, 2.12 mMol) and tris(dibenzylideneacetone)dipalladium (0) (1.29 9, 1.41 mMol) and the reaction mixture was heated to 100° C. and reacted at this temperature overnight. The mixture was then cooled to ambient temperature, filtered, and concentrated under vacuum to give an orange foam. The foam was chromatographed on flash silica gel eluting with a gradient from ethyl acetate (EtOAc)/DCM (1:5) to EtOAc/DCM (7:3) give 12.3 g of G as a slightly yellow solid.

Preparation of Compound H

{1-[2-(5-Hydroxy-benzoimidazol-1-yl)-quinolin-8-yl]-piperidin-4-yl}-carbamic acid tert-butyl ester {1-[2-(5-Methoxy-benzoimidazol-1-yl)-quinolin-8-yl]-piperidin-4-yl}-carbamic acid tert-butyl ester G (8.40 g, 17.7 mmol) was dissolved in 50 mL of trifluoroacetic acid (TFA) under an atmosphere of dry $N_2$. The reaction mixture was stirred at ambient temperature for 15 minutes after which time it was concentrated under vacuum to give a yellow oil. The oil was partitioned between DCM and 0.1N aqueous NaOH. The DCM layer was washed again with 0.1N aqueous NaOH. The DCM layer was dried over $Na_2SO_4$, filtered and concentrated to give 5.85 g of 1-[2-(5-Methoxy-benzoimidazol-1-yl)-quinolin-8-yl]-piperidin-4-ylamine as a yellow solid. C.I. m/z 374 [M+1]; $^1$H NMR ($CDCl_3$) δ 8.66 (s, 1 H), 8.37 (d, J=8.9 Hz, 1 H), 8.30 (d, J=8.7 Hz, 1 H), 7.68 (d, J=8.9 Hz, 1 H), 7.47 (m, 2 H), 7.35 (d, J=2.3 Hz, 1 H), 7.25 (m, 1 H), 7.06 (dd, J=2.5, 8.9 Hz, 1 H), 3.91 (s, 3 H), 3.88 (m, 2 H), 2.90 (m, 3 H), 2.05 (m, 2 H), 1.83 (m, 2 H), 1.50 (brs, 2 H).

1-[2-(5-Methoxy-benzoimidazol-1-yl)-quinolin-8-yl]-piperidin-4-ylamine (500 mg, 1.10 mmol) was dissolved in 10 mL of DCM under an atmosphere of dry $N_2$. To this solution was added boron tribromide (300 mL, 3.30 mmol) and the mixture was stirred overnight at ambient temperature. Then an additional 200 mL of borontribromide was added and the mixture was stirred for two hours. The reaction mixture was then poured over crushed ice and the pH of the resulting solution was adjusted to 9 with the careful addition of sodium carbonate (Na₂CO₃). The slurry was filtered and the solid was washed with water followed by Et₂O and then dried under vacuum to give 1-[8-(4-Amino-piperidin-1-yl)-quinolin-2-yl]-1H-benzoimidazol-5-ol as a yellow solid. C.I. m/z 360 [M+1]; $^1$H NMR (DMSO) δ 9.07 (s, 1 H), 8.76 (d, J=8.9 Hz, 1 H), 8.48 (d, J=8.9 Hz, 1 H), 8.10 (d, J=8.9 Hz, 1 H), 7.56 (d, J=7.4 Hz, 1 ), 7.45 (m, 1 H), 7.26 (d, J=7.4 Hz, 1 H), 7.01 (d, J=2.2 Hz, 1 H), 6.95 (dd, J=2.2, 8.9 Hz, 1 H), 3.72 (m, 2 H), 2.76 (m, 3 H), 1.88 (m, 2 H), 1.65 (m, 2 H).

1-[8-(4-Amino-piperidin-1-yl)-quinolin-2-yl]-1 H-benzoimidazol-5-ol (460 mg, 1.30 mmol) was dissolved in 5 mL of anhydrous DMF under an atmosphere of dry N₂. To this solution was added di-tert-butyldicarbonate (279 mg, 1.30 mmol) and the reaction mixture was stirred at ambient temperature overnight. The reaction mixture was then concentrated under vacuum and partitioned between DCM and aqueous saturated NaHCO₃. The DCM layer was dried over Na₂SO₄, filtered and concentrated under vacuum to give a yellow solid. The solid was chromatographed on flash silica gel eluting with EtOAc to give 273 mg of H as a yellow solid.

EXAMPLE 2

Preparation of 1-[2-(5-Cyclopropylmethoxy-benzoimidazol-1-yl)-quinolin-8-yl]-piperidin-4-ylamine {1-[2-(5-Hydroxy-benzoimidazol-1-yl)-quinolin-8-yl]-piperidin-4-yl}-carbamic acid tert-butyl ester H (200 mg, 0.435 mmol) was dissolved in 1.5 mL of anhydrous DMF under an atmosphere of dry N₂. To this solution was added Cs₂CO₃ (170 mg, 0.520 mmol) followed by cyclopropyl methane bromide (46 mL, 0.48 mMol). The reaction mixture was subsequently heated to 65° C. and stirred at this temperature for 4 hours. The reaction mixture was then cooled to ambient temperature and partitioned between EtOAc and water. The EtOAc layer was washed 4 more times with water and then with brine. The EtOAc was then dried over Na₂SO₄, filtered and concentrated under vacuum and the resulting green oil was chromatographed on flash silica gel eluting with MeOH/dichloromethane (DCM) (2:98) to give the a green oil. The oil was dissolved in 1.5 mL of TFA under an atmosphere of dry N₂. The reaction mixture was stirred at ambient temperature for 10 minutes after which time it was concentrated under vacuum and the resulting residue was partitioned between DCM and aqueous 0.1 N NaOH. The DCM layer was then washed with basic brine (pH =10), dried over Na₂SO₄, filtered and concentrated under vacuum to give 118 mg 1-[2-(5-Cyclopropyl-methoxy-benzoimidazol-1-yl)-quinolin-8-yl]-piperidin-4-ylamine as a yellow solid. C.I. m/z 414 [M+1]; $^1$H NMR (CDCl₃) δ 8.63 (s, 1 H), 8.37 (d, J=8.9 Hz, 1 H), 8.27 (d, J=8.7 Hz, 1 H), 7.65 (d, J=8.7 Hz, 1 H), 7.44 (m, 2 H), 7.30 (d, J=2.5 Hz, 1 H), 7.24 (m, 1 H), 7.09 (dd, J=2.5, 8.9 Hz, 1 H), 3.87 (m, 4 H), 2.87 (m, 3 H), 2.03 (m, 2 H), 1.81 (m, 2 H), 1.56 (brs, 2 H), 1.32 (m, 1 H), 0.66 (m, 2 H), 0.39 (m, 2 H).

EXAMPLE 3

Preparation of Besylate Salt of 1-[2-(5-Cyclopropylmethoxy-benzoimidazol-1-yl)-quinolin-8-yl]-piperidin-4-ylamine The besylate salt of 1-[2-(5-cyclopropylmethoxy-benzoimidazol-1-yl)-quinolin-8-yl]-piperidin-4-ylamine is prepared by reacting one equivalent of benezensulfonic acid with one equivalent of 1-[2-(5-cyclopropylmethoxy-benzoimidazol-1-yl)-quinolin-8-yl]-piperidin-4-ylamine. The product is recovered using any of the well-known techniques employed in the preparation of salts of organic compounds.

EXAMPLE 4

Preparation of 1-{2-[5-(3-Morpholin-4-yl-propoxy)-benzoimidazol-1-yl]-quinolin-8-yl}-piperidin-4-ylamine 1-{2-[5-(3-Morpholin4-yl-propoxy)-benzoimidazol-1-yl]-quinolin-8-yl}-piperidin-4-ylamine was prepared according to the manner described in Example 2 and was determined to have LRMS (MH+) of 487.2.

EXAMPLE 5

Preparation of 1(+)-1-{2-[5-(Tetrahydro-furan-3-yloxy)-benzoimidazol-1-yl]-quinolin-8-yl}-piperidin-4-ylamine (±)-1-{2-[5-(Tetrahydro-furan-3-yloxy)-benzoimidazol-1-yl]-quinolin-8-yl}-piperidin-4-ylamine was prepared according to the manner described in Example 2 and was determined to have LRMS (MH+) of 430.4. The racemate of 1-{2-[5-(Tetrahydro-furan-3-yloxy)-benzoimidazol-1-yl]-quinolin-8-yl}-piperidin-4-ylamine may be separated into its enantiomers using techniques well known to those of ordinary skill in the art.

EXAMPLE 6

Preparation of 1-{2-[5-(3-Methyl-oxetan-3-ylmethoxy)-benzoimidazol-1-yl]-quinolin-8-yl}-piperidin-4-ylamine 1-{2-[5-(3-Methyl-oxetan-3-ylmethoxy)-benzoimidazol-1-yl]-quinolin-8-yl}-piperidin-4-ylamine was prepared according to the manner described in Example 2 and was determined to have LRMS (MH+) of 444.4.

EXAMPLE 7

Preparation of 1-[2-(5-Isobutoxy-benzoimidazol-1-yl)-quinolin-8-yl]-piperidin-4-ylamine 1-[2-(5-Isobutoxy-benzoimidazol-1-yl)-quinolin-8-yl]-piperidin-4-ylamine was prepared according to the manner described in Example 2 and was determined to have LRMS (MH+) of 410.0.

EXAMPLE 8

Preparation of 1-{2-[5-(Tetrahydro-pyran-4-yloxy)-benzoimidazol-1-yl]-quinolin-8-yl}-piperidin-4-ylamine 1-{2-[5-(Tetrahydro-pyran-4-yloxy)-benzoimidazol-1-yl]-quinolin-8-yl}-piperidin-4-ylamine was prepared according to the manner described in Example 2 and was determined to have LRMS (MH+) of 444.4.

What is claimed is:
1. A compound selected from the group consisting of:
(±)-1-{2-[5-(Tetrahydro-furan-3-yloxy)-benzoimidazol-1-yl]-quinolin-8-yl}-piperidin-4-ylamine;

1-{2-[5-(3-Methyl-oxetan-3-ylmethoxy)-benzoimidazol-1-yl]-quinolin-8-yl}-piperidin-4-ylamine;
1-{2-[5-(Tetrahydro-pyran-4-yloxy)-benzoimidazol-1-yl]-quinolin-8-yl}-piperidin-4-ylamine; and the pharmaceutically acceptable salts of the foregoing compounds.

2. A compound according to claim 1 selected from the group consisting of:
(+)-1-{2-[5-(Tetrahydro-furan-3-yloxy)-benzoimidazol-1-yl]-quinolin-8-yl}-piperidin-4-ylamine;
(−)-1-{2-[5-(Tetrahydro-furan-3-yloxy)-benzoimidazol-1-yl]-quinolin-8-yl}-piperidin-4-ylamine; and the pharmaceutically acceptable salts of the foregoing compounds.

3. A compound according to claim 1, selected from the group consisting of:
1-{2-[5-(3-Methyl-oxetan-3-ylmethoxy)-benzoimidazol-1-yl]-quinolin-8-yl}-piperidin-4-ylamine; and the pharmaceutically acceptable salts compound.

4. A compound according to claim 1, selected from the group consisting of:
1-{2-[5-(Tetrahydro-pyran-4-yloxy)-benzoimidazol-1-yl]-quinolin-8-yl}-piperidin-4-ylamine; and the pharmaceutically acceptable salts compound.

5. A compound according to claim 1, wherein said salt is the benzenesulfonate salt.

6. A compound according to claim 2, wherein said salt is the benzenesulfonate salt.

7. A compound according to claim 3, wherein said salt is the benzenesulfonate salt.

8. A compound according to claim 4, wherein said salt is the benzenesulfonate salt.

9. A pharmaceutical composition comprising an amount of a compound of claim 1 that is effective in treating abnormal cell growth, and a pharmaceutically acceptable carrier.

* * * * *